(12) United States Patent
Klapproth

(10) Patent No.: US 7,563,762 B2
(45) Date of Patent: Jul. 21, 2009

(54) COMPOSITION AND PROCESS FOR STABILIZING OF BIOMOLECULES

(75) Inventor: Holger Klapproth, Freiburg (DE)

(73) Assignee: Micronas GmbH, Freiburg (DE)

( * ) Notice: Subject to any disclaimer, the term of this patent is extended or adjusted under 35 U.S.C. 154(b) by 43 days.

(21) Appl. No.: 10/520,158

(22) PCT Filed: Jul. 4, 2003

(86) PCT No.: PCT/DE03/02245

§ 371 (c)(1), (2), (4) Date: Jan. 4, 2005

(87) PCT Pub. No.: WO2004/004455

PCT Pub. Date: Jan. 15, 2004

(65) Prior Publication Data

US 2006/0172928 A1    Aug. 3, 2006

(30) Foreign Application Priority Data

Jul. 4, 2002  (FR) ................................. 102 30 210

(51) Int. Cl.
- *A61K 38/00* (2006.01)
- *A61K 9/16* (2006.01)
- *A61K 31/715* (2006.01)
- *C12P 19/12* (2006.01)

(52) U.S. Cl. ............... 514/2; 514/53; 514/56; 530/327; 424/1.69; 435/100

(58) Field of Classification Search ....................... None
See application file for complete search history.

(56) References Cited

U.S. PATENT DOCUMENTS 5,624,831 A    4/1997   Vu Khue et al.

OTHER PUBLICATIONS

Oliver et al. "Non-Disaccharide-Based Mechanisms of Protection During Drying." Cryobiology, 2001, 43, 151.*

Nguyen et al. "Protection of immunoreactivity of dry immobilized proteins on microtitration plates in ELISA: application for detection of autoantibodies in Myasthenia gravis," J. Biotech., 1999, 72, 115-25.*

Browne et al. "Plant desiccation gene found in a nematode," Nature, 2002, 416, 38.*

Ann E. Oliver et al., Non-Disaccharide-Based Mechanisms of Protection During Drying, Cryobioolgy 43, www.academicpress.com, 2001, pp. 151-167.

V.K. Nguyen et al., Protection of Immunoreactivity of Dry Immobolized Proteins on Microtitration Plates in Elisa: Application for Detection of Autoantibodies in Myasthenia Gravis, 1: J Biotechnol 1999, 72(1-2):115-25. Abstract only.

Ingram J. Bartels, The Molecular Basis of Dehydration Tolerance Inplants, Annu Rev Plant Physiol Plant Mol Biol, 1996, 47:377-403. Abstract only.

J. Brown et al., Plant Desiccation Gene Found in a Nematode, Nature, www.nature.com, 2002, vol. 416.

Solomon, A et al., Desiccation Stress of Entomopathogenic Nematodes Induces the Accumulation of a Novel Heat-Stable Protein, Parasitology, 2000, 121 (Pt 4):409-16. Abstract only.

Kurt Sales et al., The Lea-Like Protein HSP 12 in *Saccharomyces cerevisiae* has a Plasma Membrane Location and Protects Membranes Against Desiccation and Ethanol-Induced Stress, Biochimica et Biophysica Acta 1463, 2000, 267-278.

Ried JL, Walker-Simmons MK, Group 3 Late Embryogenisis Abundant Proteins in Desiccation-Tolerant Seedlings of Whest (Triticum Astivum L.), Plant Physiol, 1993, 102 (1):125-131. Abstract only.

Willem F. Wolkers et al., Isolation and Characterization of a D-7 Lea Protein From Pollen That Stabilizes Glasses in Vitro, Biochimica et Biophysica Acta 1544, 2001, 196-206.

* cited by examiner

*Primary Examiner*—Cecilia Tsang
*Assistant Examiner*—Maury Audet
(74) *Attorney, Agent, or Firm*—Biotech Beach Law Group, PC; Raymond Wagenknecht

(57) ABSTRACT

The present invention relates in general to the field of biotechnology. The invention particularly relates to a composition and process for stabilizing or preserving biological molecules, as well as devices that comprise correspondingly stabilized or preserved biomolecules.

7 Claims, No Drawings

SEQUENCE LISTING

<160> NUMBER OF SEQ ID NOS: 9

<210> SEQ ID NO 1
<211> LENGTH: 11
<212> TYPE: PRT
<213> ORGANISM: Artificial sequence
<220> FEATURE:
<223> OTHER INFORMATION: Description of the artificial sequence: Motif
      of the LEA class
<220> FEATURE:
<223> OTHER INFORMATION: Amino acid position 1: X= K or T
<220> FEATURE:
<223> OTHER INFORMATION: Amino acid position 2: X=A or G or K or M or T
<220> FEATURE:
<223> OTHER INFORMATION: Amino acid position 3: X=R or D or A or E or Q
      or K
<220> FEATURE:
<223> OTHER INFORMATION: Amino acid position 4: X= E or K or S
<220> FEATURE:
<223> OTHER INFORMATION: Amino acid position 5: X= T or F or Y or A
<220> FEATURE:
<223> OTHER INFORMATION: Amino acid position 6: X= K or R or T or A
<220> FEATURE:
<223> OTHER INFORMATION: Amino acid position 7:  X= D or E or Q
<220> FEATURE:
<223> OTHER INFORMATION: Amino acid position 8: X= S or R or Y or K

```
<220> FEATURE:
<223> OTHER INFORMATION: Amino acid position 9: X= A or T
<220> FEATURE:
<223> OTHER INFORMATION: Amino acid position 10: X= G or A or R

<400> SEQUENCE: 1

Xaa Xaa Xaa Xaa Xaa Xaa Xaa Xaa Xaa Xaa Glu
 1               5                  10

<210> SEQ ID NO 2
<211> LENGTH: 11
<212> TYPE: PRT
<213> ORGANISM: Aphelenchus avenae

<400> SEQUENCE: 2

Lys Thr Ala Glu Phe Arg Asp Ser Ala Gly Glu
 1               5                  10

<210> SEQ ID NO 3
<211> LENGTH: 11
<212> TYPE: PRT
<213> ORGANISM: Aphelenchus avenae

<400> SEQUENCE: 3

Lys Gly Gln Glu Phe Lys Glu Arg Ala Gly Glu
 1               5                  10

<210> SEQ ID NO 4
<211> LENGTH: 11
<212> TYPE: PRT
<213> ORGANISM: Aphelenchus avenae

<400> SEQUENCE: 4

Lys Ala Glu Glu Thr Lys Gln Arg Ala Gly Glu
 1               5                  10

<210> SEQ ID NO 5
<211> LENGTH: 11
<212> TYPE: PRT
<213> ORGANISM: Aphelenchus avenae

<400> SEQUENCE: 5

Lys Met Asp Glu Thr Lys Gln Arg Ala Gly Glu
 1               5                  10

<210> SEQ ID NO 6
<211> LENGTH: 11
<212> TYPE: PRT
<213> ORGANISM: Betula pendula

<400> SEQUENCE: 6

Lys Ala Arg Lys Thr Lys Asp Ser Ala Ala Glu
 1               5                  10

<210> SEQ ID NO 7
<211> LENGTH: 11
<212> TYPE: PRT
<213> ORGANISM: Betula pendula

<400> SEQUENCE: 7

Lys Ala Lys Glu Tyr Lys Asp Tyr Thr Ala Glu
 1               5                  10

<210> SEQ ID NO 8
<211> LENGTH: 11
```

-continued

```
<212> TYPE: PRT
<213> ORGANISM: Betula pendula

<400> SEQUENCE: 8

Lys Ala Arg Glu Thr Thr Glu Lys Ala Arg Glu
 1               5                  10

<210> SEQ ID NO 9
<211> LENGTH: 11
<212> TYPE: PRT
<213> ORGANISM: Betula pendula

<400> SEQUENCE: 9

Thr Lys Asp Ser Ala Ala Glu Lys Ala Arg Glu
 1               5                  10
```

COMPOSITION AND PROCESS FOR STABILIZING OF BIOMOLECULES

This application is the U.S. National Stage Entry of International Application No. PCT/DE 03/02245, filed Jul. 4, 2003, which claims priority to German Application No. DE 102 30 210.3, filed Jul. 4, 2002. The present application incorporates herein the full disclosures of both the International Application No. PCT/DE 03/02245 and the German Application No. 102 30 210.3.

This application incorporates by reference the Sequence Listing on the compact disc, namely the file "SEQUENCE LISTING.txt" created on Oct. 11, 2005 with a size of 2,837 bytes.

FIELD OF THE INVENTION

The present invention relates generally to the field of biotechnology. In particular, the invention relates to a composition and process for stabilizing, or, as the case may be, preserving biological molecules as well as devices that comprise the correspondingly stabilized biomolecules.

BACKGROUND OF THE INVENTION

The use of proteins and polypeptides in industrial products and processes requires large quantities of these biomolecules, in particular for clinical/diagnostic and pharmaceutical purposes. Whereas the required basic techniques such as isolation and purification of proteins in industrial quantities are mostly established, the most difficult aspect of the use of such biomolecules resides in maintenance for the envisioned application, of the desired native, or, active molecular properties. Particularly, in the storage and transport of biomolecules, losses in activity often have to be taken into account, whereby the success of later applications is put in risk. Commercially obtainable protein preparations therefore for the most part comprise compounds whose presence can minimize the activity loss during storage or transport. Furthermore, storage and transport is mostly carried out under low temperatures, although a freezing of, for example, particular proteins may be undesirable because of molecular changes.

It is known from the literature that particular plants and animals have developed mechanisms to survive in the state of approaching complete dehydration. This state of stress is referred to anhydrobiosis and is observed in organisms that are exposed to dry conditions. During anhydrobiosis, the organism finds itself in a kind of resting state until a rehydration allows normal metabolism to continue. Common characteristic property of these organisms is the synthesis of high concentrations of non-reducing sugars that is induced during anhydrobiotic conditions. The observed accumulation of large quantities of trehalose as a response to dehydration in various organisms leads to a protection of membranes and proteins from damage to their molecular integrity and correlates to a certain tolerance with respect to water removal. One assumes that the sugar replaces, or, as the case may be, functionally substitutes the removed water molecules and is involved in the formation of an intracellular organic glass by which, one assumes, the cell contents are stabilized.

In the state of the art, the use of trehalose in the production of antibody-coated microtiter plates is described in order to stabilize this normally very quickly denatureable protein species (V. K. Nguyen et al., Protection of immunoreactivity of dry immobilized proteins on microtitration plates in ELISA: application for detection of autoantibodies in *Myasthenia gravis*, *J. of Biotechnology*, 72, pp. 115 to 125 (1999)). In this case, microtiter plates having antibodies immobilized thereon are covered with a bovine serum albumin (BSA) and trehalose-containing film and are thereafter dried. The immobilized dried antibodies of the ELISA plates made in this manner showed a storage capability of up to thirty days even at increased temperatures (up to 50° C.).

An increase of the storage capability, particularly from a commercial viewpoint, at room temperature or even tropical conditions can, however, not be achieved with this technology. Particularly in connection with the preparation of large quantities of immobilized proteins, it is desirable to have a storage capability for a time period of over a year with substantially constant biological activity, or functionality of the biomolecule.

A further disadvantage of the above-described technology lies in the use of bovine serum albumin (BSA), a protein mixture of which it is known that, in the framework of antibody-aided applications, unspecific binding with antibodies results and thereby creates undesired cross reactions through which the entire experimental result is negatively influenced.

It is known, particularly from plant seeds and pollen that, in reaction to water removal, proteins of the LEA class are formed in them. (LEA='late embryogenesis abundant') (J. Ingram and D. Bartels, *Annu. Rev. Plant Physiol. Plant Mol. Biol.*, 47 pp. 377-403 (1996)). The LEA proteins also identified in nematodes, comprise a special, 11 amino acid motif, which presumably forms an amphipathic α-Helix through which the oligomerization of the protein is controlled. The LEA proteins are extremely hydrophilic and resistant to denaturation by heat. Initial experiments with a protein of this class purified from the pollen of *Typha latifolia* have shown that, in vitro, sucrose glasses can be stabilized by incubation with this protein. It is therefore suspected that non-reducing sugars and representatives of the protein class LEA work together in a synergistic manner in the formation of a stable bioglass in the cytoplasma of anhydrobiotic plants and in seeds and pollen being resistant to desiccation (J. Brown et al, Plant desiccation gene found in a nematode, *Nature*, 416, p. 38 (2002)).

An object of the present invention is therefore the provision of compositions and processes for stabilizing, or, as the case may be, preserving biomolecules, by which the disadvantages of the state of the art are overcome, and with which the desired biological activity of the molecules can be preserved, even without cooling, over a longer period of time.

The object is solved according to the present invention by the composition according to the main claim.

SUMMARY OF THE INVENTION

The composition according to the present invention comprises at least one non-reducing disaccharide, selected from the group consisting of trehalose (D-glucopyranosyl-D-glucopyranose), sucrose (β-D-fructofuranosyl-α-D-glucopyranoside), as well as derivatives thereof, and at least one protein or polypeptide of the LEA class.

DETAILED DESCRIPTION OF ILLUSTRATIVE EMBODIMENTS OF THE INVENTION

According to a preferred embodiment, the composition according to the present invention comprises trehalose as well as at least one protein or polypeptide of the LEA class with an 11 amino acid motif, characterized by the following general formula (SEQ ID NO. 1):

(1)-(2)-(3)-(4)-(5)-(6)-(7)-(8)-(9)-(10)-E, wherein
   (1) signifies K or T,
   (2) signifies A, G, K, M or T,
   (3) signifies R, D, A, E, Q or K,
   (4) signifies E, K or S,
   (5) signifies T, F, Y or A,
   (6) signifies K, R, T or A, (7) signifies D, E or Q,
(8) signifies S, R, Y or K,
(9) signifies A or T, and
(10) signifies G, A or R.

In a particularly preferred embodiment, the composition comprises at least one protein or polypeptide of the LEA subclass 3 having an amino acid sequence that is coded by a nucleotide sequence as deposited in the GenBank under the accession number AF423069 or S39475.

The composition according to the present invention comprises, as particularly preferred, at least one protein or polypeptide of the LEA subclass 3 with an 11 amino acid motif, selected from the group consisting of:

(a) K-T-A-E-F-R-D-S-A-G-E (SEQ ID NO. 2), (b) K-G-Q-E-F-K-E-R-A-G-E (SEQ ID NO. 3), (c) K-A-E-E-T-K-Q-R-A-G-E (SEQ ID NO. 4), (d) K-M-D-E-T-K-Q-R-A-G-E (SEQ ID NO. 5), (e) K-A-R-K-T-K-D-S-A-A-E (SEQ ID NO. 6), (f) K-A-K-E-Y-K-D-Y-T-A-E (SEQ ID NO. 7), (g) K-A-R-E-T-T-E-K-A-R-E (SEQ ID NO. 8), and (h) T-K-D-S-A-A-E-K-A-R-E (SEQ ID NO. 9).

According to a preferred embodiment, the composition comprises the components of the non-reducing disaccharide and the protein or polypeptide of the LEA class in respective quantities of from 0.01 to 15, or, 0.00001 to 1 weight percent, respectively, with reference to a ready-to-use solution.

For example, the composition is produced by adding 0.1 weight percent of a purified LEA protein and 5 weight percent trehalose to a solution of 50 mM phosphate and 100 mM NaCl with a pH value of 6.8. If desirable, further components such as, for example, sodium azide (0.02 weight percent) can also be added.

It is clear to one of skill in the art that by means of the sequence and motif information homologues representatives of the protein class LEA from different sources can be obtained and applied according to the present invention. As follows, all homologs are included, so far as they can stabilize a biological glass formed from non-reducing sugars, such as, in particular, trehalose and/or sucrose.

Exemplary representatives of the protein class LEA are presented in the following table, however these examples do not limit the present invention. The respective sequence information can easily be obtained by one of skill in the art by means of the presented data.

| Data bank | Organism | Reference (Accession No.) |
| --- | --- | --- |
| SWISS-PROT | Gossypium hirsutum | P09422 |
| SWISS-PROT | Raphanus sativus | P21208 |
| SWISS-PROT | Zea mays | P46517 |
| SWISS-PROT | Hordeum vulgare | Q02400 |
| SWISS-PROT | Hordeum vulgare | Q05191 |
| SWISS-PROT | Hordeum vulgare | Q5190 |
| SWISS-PROT | Hordeum vulgare | P46532 |
| SWISS-PROT | Helianthus annuus | P46515 |
| SWISS-PROT | Helianthus annuus | P46515 |
| SWISS-PROT | Gossypium hirsutum | P09411 |
| SWISS-PROT | Gossypium hirsutum | P46518 |
| SWISS-PROT | Gossypium hirsutum | P09443 |
| SWISS-PROT | Gossypium hirsutum | P13940 |
| SWISS-PROT | Gossypium hirsutum | P09444 |
| SWISS-PROT | Gossypium hirsutum | P46521 |

-continued

| Data bank | Organism | Reference (Accession No.) |
| --- | --- | --- |
| SWISS-PROT | Gossypium hirsutum | P4522 |
| SWISS-PROT | Brassica napus | P13934 |
| SWISS-PROT | Gossypium hirsutum | P13939 |
| SWISS-PROT | Zea mays | Q42376 |
| SWISS-PROT | Tricitum aestivum | Q03968 |
| TrEMBL | Phaseolus vulgaris | O24442 |
| TrEMBL | Arabidopsis thaliana | O64820 |
| TrEMBL | Arabidopsis thaliana | O65148 |
| TrEMBL | Arabidopsis thaliana | O80576 |
| TrEMBL | Arabidopsis thaliana | O81483 |
| TrEMBL | Oryza sativa | P83196 |
| TrEMBL | Oryza sativa | P83197 |
| TrEMBL | Glycine max | P93165 |
| TrEMBL | Glycine max | Q01527 |
| TrEMBL | Tricitum aestivum | Q03967 |
| TrEMBL | Arabidopsis thaliana | Q39138 |
| TrEMBL | Citrus sinensis | Q39466 |
| TrEMBL | Chlorella vulgaris | Q39660 |
| TrEMBL | Gossypium hirsutum | Q39793 |
| TrEMBL | Gossypium hirsutum | Q39797 |
| TrEMBL | Glycine soja | Q39919 |
| TrEMBL | Onoclea sensibilis | Q40697 |
| TrEMBL | Picea glauca | Q40842 |
| TrEMBL | Picea glauca | Q40843 |
| TrEMBL | Picea glauca | Q40848 |
| TrEMBL | Picea glauca | Q40858 |
| TrEMBL | Picea glauca | Q40869 |
| TrEMBL | Zea mays | Q41804 |
| TrEMBL | Oryza sativa | Q8S4X7 |
| TrEMBL | Brassica campestris | Q8S8Z2 |
| TrEMBL | Brassica napus | Q8S8Z2 |
| TrEMBL | Arabidopsis thaliana | Q96273 |
| TrEMBL | Oryza sativa | Q9AWZ5 |
| TrEMBL | Arabidopsis thaliana | Q9FG31 |
| TrEMBL | Arabidopsis thaliana | Q9FK14 |
| TrEMBL | Arabidopsis thaliana | Q9FK15 |
| TrEMBL | Arabidopsis thaliana | Q9FKV7 |
| TrEMBL | Oryza sativa | Q9FPB2 |
| TrEMBL | Arabidopsis thaliana | Q9LF88 |
| TrEMBL | Oryza sativa | Q9LGL8 |
| TrEMBL | Arabidopsis thaliana | Q9LT74 |
| TrEMBL | Euphorbia esula | Q9M556 |
| TrEMBL | Arabidopsis thaliana | Q9S7S3 |
| TrEMBL | Oncolea sensibilis | Q9S2B2 |
| TrEMBL | Arabidopsis thaliana | Q9SKPO |
| TrEMBL | Chlorella vulgaris | Q9SLP7 |
| TrEMBL | Arabidopsis thaliana | Q9XID7 |
| TrEMBL | Arabidopsis thaliana | Q9ZPW6 |
| TrEMBL | Glycine max | Q9ZTZ2 |

The LEA proteins or polypeptides proposed according to the present invention can be isolated from natural sources, produced recombinantly or synthesized. The processes to be used are well known to one of ordinary skill in the art.

A further aspect of the present invention relates to the provision of a method for stabilizing or preserving biomolecules in which the molecules to be protected are incubated in the composition according to the present invention. After a sufficient period of incubation, the preparation can then, for example, be dried at room temperature and stored until use without cooling. Insofar as the process is used for stabilization of biomolecules immobilized on particular surfaces, these loaded surfaces are covered with the composition according to the present invention. This can, for example, take place by spraying the composition on the surface or by immersing the surface in the composition. In the case of an immersion method, the surface should, preferably, be withdrawn with a speed of about 2 mm per second so that a uniform wetting with the composition according to the present invention can take place.

A further aspect of the present invention relates to the provision of surfaces that have been covered with the composition of the present invention. Biomolecules are directly or indirectly immobilized on preferred surfaces and are stabilized or preserved with the composition of the present invention. Particularly preferred surfaces are components of analytical and/or diagnostic devices, such as, for example, biochips, sensor chips, microtiter plates, test tubes, and the like. The material of the surface is not limited and can, for example be selected from glass, quartz glass, quartz, silicon, polymers (PMMA, polystyrene, polyethylene, polypropylene, PVC, etc.), and membranes such as, for example, nitrocellulose, nylon and microfiber membranes, as well as paper.

The terms "stabilization" and "preservation" as used herein, relate to the structural or functional integrity of biomolecules and the biological properties based thereon. The required activity of a biomolecule for a particular application requires, for example, the significant conservation of its primary, secondary and/or tertiary structure. The biological activity of a nucleic acid probe comprises, for example, its property for forming a hybridization complex with a nucleic acid target which is complementary to the probe. The biological activity of an antibody comprises, for example, a specific binding of an antigen.

It is clear to one of skill in the art that the composition and processes according to the present invention can also be applied to cellular tissues and complete cells as well as portions thereof (organelles, membranes and membrane fragments, etc.) as long as they are carriers of the above biomolecules. For this reason, tissues, cells and portions thereof are basically encompassed by the term "biomolecules".

The presently used term "biological molecule" and "biomolecule" encompass any substances and compounds substantially of biological origin that have properties that are relevant within the framework of scientific, diagnostic and/or pharmaceutical applications. Encompassed are not only native molecules, such as those that can be isolated from natural sources, but also forms, fragments and derivatives derived therefrom, as well as recombinant forms and artificial molecules, as long as at least one property of the native molecules is present. Preferred biomolecules are those that can be applied for analytical, diagnostic and/or pharmaceutical purposes, such as nucleic acids and their derivatives (DNA, RNA, PNA, LNA, ribozymes, oligonucleotides, plasmids, chromosomes), peptides and proteins (enzymes, receptor proteins, protein complexes, peptide hormones, antibodies), as well as biologically active fragments thereof, carbohydrates and their derivatives such as, in particular, glycosylated proteins and glycosides, and fats, fatty acids and lipids.

The invention is more closely elucidated by means of the following example.

Coating of Surfaces

The formation of a composition according to the present invention results by dissolving 0.1% (weight/volume) recombinant LEA-protein and 5% (weight/volume) trehalose and 100 ml phosphate buffer (50 mM phosphate, 100 mM NaCl, pH 6.8). Subsequently, 0.02% (weight/volume) sodium azide is added as a cytotoxic agent against microbial impurities. After sterile filtration of the solution obtained using a 0.2 micrometer filter, the result is stored in an autoclaved sterile bottle.

In order to layer suitable surfaces according to the present invention, biochips (for example microscope slides) with immobilized biomolecules are immersed in the solution in a clean room (or sterile work bench) and are drawn out of the solution with a speed of 2 mm per second. In this manner a thin layer of the trehalose/LEA solution is dried on the chip and leads to the stabilization of the biomolecules.

For storage, the chips with stabilized biomolecules treated in this manner can be packaged in plastic bags and stored at room temperature under an atmosphere of nitrogen. The bags can preferably be packed in a carton sealed from light in order to prevent possible photo degradation of the proteins.

For use, the chips are taken from their packaging and rehydrated (5 minutes, RT) with assay buffer (for example PBS buffer). Next, the sample liquid is incubated directly on the chip and the assay is carried out. All kinds of receptor ligand interactions known in the art can be carried out. If desired the removal of the stabilizer can also be left out. In this case the sample is directly put onto the trehalose layered surface. This is above all practical if it has been previously shown that neither trehalose nor LEA protein interfere with the detection.

The invention claimed is:

1. A process for stabilizing or preserving a biomolecule comprising the steps of:
 (a) providing a biomolecule immobilized on a surface; and
 (b) covering the surface with a composition comprising:
  i. at least one non-reducing disaccharide selected from the group consisting of trehalose (D-glucopyranosyl-D-glucopyranoside), sucrose (β-D-fructofuranosyl-α-D-glucopyranoside), and a derivative thereof; and
  ii. at least one protein or polypeptide of the Late Embryogenesis Abundant (LEA) class comprising a motif comprising 11 amino acids, wherein the motif is selected from the group consisting of:

(a) K-T-A-E-F-R-D-S-A-G-E (SEQ ID NO. 2),
   (b) K-G-Q-E-F-K-E-R-A-G-E (SEQ ID NO. 3),
   (c) K-A-E-E-T-K-Q-R-A-G-E (SEQ ID NO. 4),
   (d) K-M-D-E-T-K-Q-R-A-G-E (SEQ ID NO. 5),
   (e) K-A-R-K-T-K-D-S-A-A-E (SEQ ID NO. 6),
   (f) K-A-K-E-Y-K-D-Y-T-A-E (SEQ ID NO. 7),
   (g) K-A-R-E-T-T-E-K-A-R-E (SEQ ID NO. 8), and
   (h) T-K-D-S-A-A-E-K-A-R-E (SEQ ID NO. 9).

2. A process according to claim 1, wherein said non-reducing disaccharide is present at from 0.01 to 15 weight percent in relation to a ready-to-use solution and said protein or polypeptide of the LEA class is present at from 0.00001 to 1 weight percent in relation to the ready-to-use solution.

3. A process for the production of a surface with an immobilized and stabilized or preserved biomolecule, comprising the steps of:
 (a) providing a surface with a biomolecule immobilized thereon; and
 (b) covering the biomolecule with a composition comprising:
  i. at least one non-reducing disaccharide selected from the group consisting of trehalose (D-glucopyranosyl-D-glucopyranoside), sucrose (β-D-fructofuranosyl-α-D-glucopyranoside), and a derivative thereof; and
  ii. at least one protein or polypeptide of the (LEA) class comprising a motif comprising 11 amino acids, wherein the motif is selected from the group consisting of:

(a) K-T-A-E-F-R-D-S-A-G-E (SEQ ID NO. 2),
   (b) K-G-Q-E-F-K-E-R-A-G-E (SEQ ID NO. 3),
   (c) K-A-E-E-T-K-Q-R-A-G-E (SEQ ID NO. 4),
   (d) K-M-D-E-T-K-Q-R-A-G-E (SEQ ID NO. 5),
   (e) K-A-R-K-T-K-D-S-A-A-E (SEQ ID NO. 6),
   (f) K-A-K-E-Y-K-D-Y-T-A-E (SEQ ID NO. 7),
   (g) K-A-R-E-T-T-E-K-A-R-E (SEQ ID NO. 8), and
   (h) T-K-D-S-A-A-E-K-A-R-E (SEQ ID NO. 9).

4. A surface of a material selected from the group consisting of glass, quartz glass, quartz, silicon, polymers, nitrocellulose, nylon and micro fiber membranes, and paper, wherein the surface includes a biomolecule immobilized thereon, covered with a stabilizing or preserving composition comprising:
 at least one non-reducing disaccharide selected from the group consisting of trehalose (D-glucopyranosyl-D-glucopyranoside), sucrose (β-D-fructofuranosyl-α-D-glucopyranoside), and a derivative thereof; and
 at least one protein or polypeptide of the LEA class comprising a motif comprising 11 amino acids, wherein the motif is selected from the group consisting of:

(a) K-T-A-E-F-R-D-S-A-G-E   (SEQ ID NO. 2),
   (b) K-G-Q-E-F-K-E-R-A-G-E   (SEQ ID NO. 3),
   (c) K-A-E-E-T-K-Q-R-A-G-E   (SEQ ID NO. 4),
   (d) K-M-D-E-T-K-Q-R-A-G-E   (SEQ ID NO. 5),
   (e) K-A-R-K-T-K-D-S-A-A-E   (SEQ ID NO. 6),
   (f) K-A-K-E-Y-K-D-Y-T-A-E   (SEQ ID NO. 7),
   (g) K-A-R-E-T-T-E-K-A-R-E   (SEQ ID NO. 8), and
   (h) T-K-D-S-A-A-E-K-A-R-E   (SEQ ID NO. 9).

5. A surface according to claim 4, wherein said non-reducing disaccharide is present at from 0.01 to 15 weight percent in relation to a ready-to-use solution and said protein or polypeptide of the LEA class is present at from 0.00001 to 1 weight percent in relation to the ready-to-use solution.

6. An analytical and/or diagnostic device, comprising a surface as defined in claim 4.

7. A device according to claim 6 selected from the group consisting of biochips, sensor chips, microtiter plates, test tubes and culture dishes.

\* \* \* \* \*